United States Patent [19]

Iida

[11] Patent Number: 5,457,502
[45] Date of Patent: Oct. 10, 1995

[54] LENS FOR EYEGLASSES IN WHICH PLURALITY OF LENSES FORMED OF CURVED SURFACE ARE COUPLED INTEGRALLY

[75] Inventor: Yoshiaki Iida, Katano, Japan

[73] Assignee: Cateye Co., Ltd., Osaka, Japan

[21] Appl. No.: 118,457

[22] Filed: Sep. 8, 1993

[30] Foreign Application Priority Data

Sep. 16, 1992 [JP] Japan ................. 4-064557 U

[51] Int. Cl.$^6$ ................. G02C 7/02; G02C 7/10
[52] U.S. Cl. ................. 351/44; 351/41; 351/62; 351/159; 2/447; D16/313
[58] Field of Search ................. 2/431, 432, 439, 2/447; D16/100, 101, 102, 111, 112, 107, 115, 116, 117, 120, 121, 122, 310, 312, 313, 314, 317, 325, 326, 340; 351/41, 44, 45, 54, 55, 62, 84, 85, 154, 159, 163, 164, 165, 168, 172

[56] References Cited

U.S. PATENT DOCUMENTS

| | | | |
|---|---|---|---|
| 1,991,544 | 2/1935 | Courmettes | 351/168 |
| 2,139,275 | 12/1938 | Lee | 2/13 |
| 2,256,966 | 9/1941 | Simonten | 2/12 |
| 2,276,102 | 3/1942 | Schwartz | 351/86 |
| 2,645,774 | 7/1953 | Dale, Jr. | 2/12 |
| 3,133,982 | 5/1964 | Janz | 351/62 |
| 3,826,564 | 7/1974 | Werling, Sr. | 351/165 X |
| 4,859,048 | 8/1989 | Jannard | 351/159 |
| 4,964,714 | 10/1990 | Weymouth, Jr. et al. | 351/62 |

FOREIGN PATENT DOCUMENTS

| | | | |
|---|---|---|---|
| 685935 | 4/1930 | France . | |
| 827548 | 1/1938 | France . | |
| 2617294 | 12/1988 | France . | |
| 0193713 | 8/1989 | Japan | 351/44 |
| 649245 | 1/1951 | United Kingdom . | |

OTHER PUBLICATIONS

Bugbee, L. W. and L. W. Bugbee Jr., *Bifocals* Onepiece Bifocal Lens Co., Indianapolis, Ind. 1923, pp. 8–14.
European Search Report dated Nov. 26, 1993.

*Primary Examiner*—William L. Sikes
*Assistant Examiner*—David R. Parsons
*Attorney, Agent, or Firm*—Banner & Allegretti, Ltd.

[57] ABSTRACT

Upper lens formed of a portion of a sphere having radius $R_2$ and lower lens formed of a portion of a sphere having radius $R_1$ are manufactured integrally by molding for forming the lens of eyeglasses Radii $R_1$ and $R_2$ are slightly different from each other, so that the front view comes into eyes through lower lens when the user is in a normal posture, while the front view comes into eyes through upper lens when the user bends forward.

5 Claims, 7 Drawing Sheets

LENS FOR EYEGLASSES IN WHICH PLURALITY OF LENSES FORMED OF CURVED SURFACE ARE COUPLED INTEGRALLY

BACKGROUND OF THE INVENTION

1. Field of the Invention

The present invention relates to eyeglasses, and more particularly to a lens of eyeglasses for use in sports such as bicycle road racing.

2. Description of the Background Art

FIG. 8 is a perspective view showing eyeglasses for use in sports being actually worn by a person, which is disclosed in U.S. Pat. No. 4,859,048, and FIG. 9 is a view seen in the direction of arrows "c" in FIG. 8.

Referring to these figures, a lens 32 for eyeglasses affixed on a frame 33 is made of, for example, an integral transparent plastic as shown in FIG. 10, and its curved surface is formed of a part of the curved outer surface of a cylinder having a radius R. Therefore, eyeglasses 34 can serve as sunglasses for use in sports securing a wide view through lens 32.

In conventional eyeglasses as mentioned above, the field of vision through lens 32 does not come into question because the line-of-sight of a person is in the direction of the arrow in solid line in FIG. 9 in the normal usage. A person, however, sometimes bends forward to look ahead during the use. In this case, the line-of-sight is in the direction of the arrow in broken line in FIG. 9, and accordingly the line-of-sight is interrupted by the structure of a frame 33, so that a sufficient front view cannot be secured. Therefore, capability of assuring safety by sight is reduced especially when a bicycle is running at high speed with a person bent forward.

SUMMARY OF THE INVENTION

An object of the present invention is to widen the front view of a lens for eyeglasses.

Another object of the present invention is to secure the field of vision efficiently in a lens for eyeglasses.

In order to achieve the above objects, a lens for eyeglasses according to the present invention includes a first lens formed of a first curved surface and a second lens formed of a second curved surface, and the first lens and the second lens are coupled integrally on a curved line where respective curved surfaces meet.

In the lens for eyeglasses structured as above, the front view is widened and the field of vision can be secured efficiently because the first lens and the second lens, which are formed of, the curved surface respectively, are coupled integrally.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
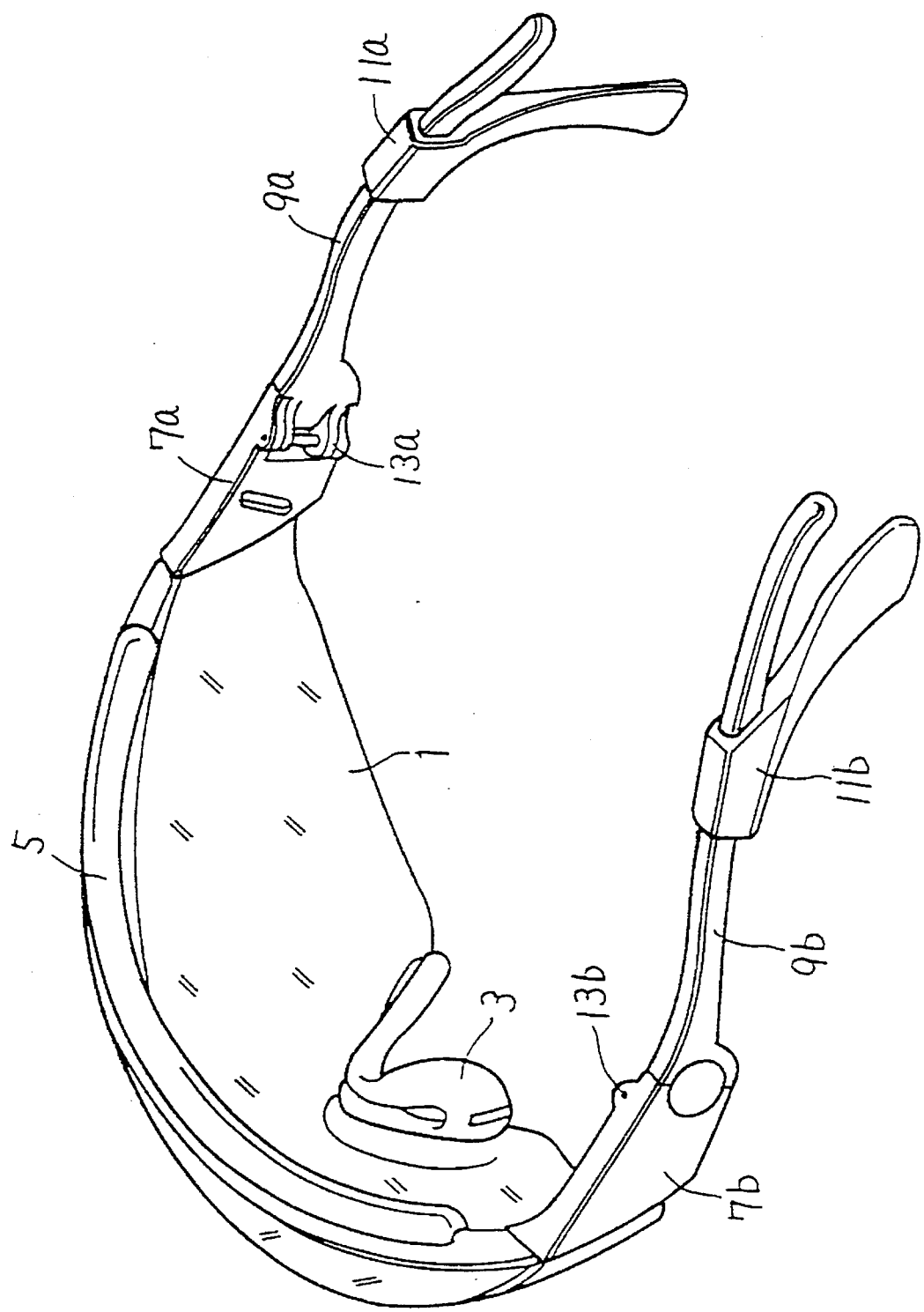
FIG. 1 is a perspective view showing an outside structure of eyeglasses according to one embodiment of the present invention.

FIG. 1 is a perspective view showing an outside structure of eyeglasses according to one embodiment of the present invention.

Referring to the figure, a nose piece 3 which can be fixed adjustably in accordance with the height of nose of a user, a pad 5 which is made of a resilient material and prevents inflow of wind from a space between the eyeglasses and a forehead during running, and support portions 7a and 7b for fixing temples, are mounted to a lens 1 having a spherical shape and made of a transparent material. Bar-shaped temples 9a and 9b which extend backwardly via hinge portions 13a and 13b are affixed rotatably to each of support portions 7a and 7b. Ear hooks 11a and 11b made of, for example, synthetic rubber are fitted slidably to temples 9a and 9b, respectively.

Figure 2:
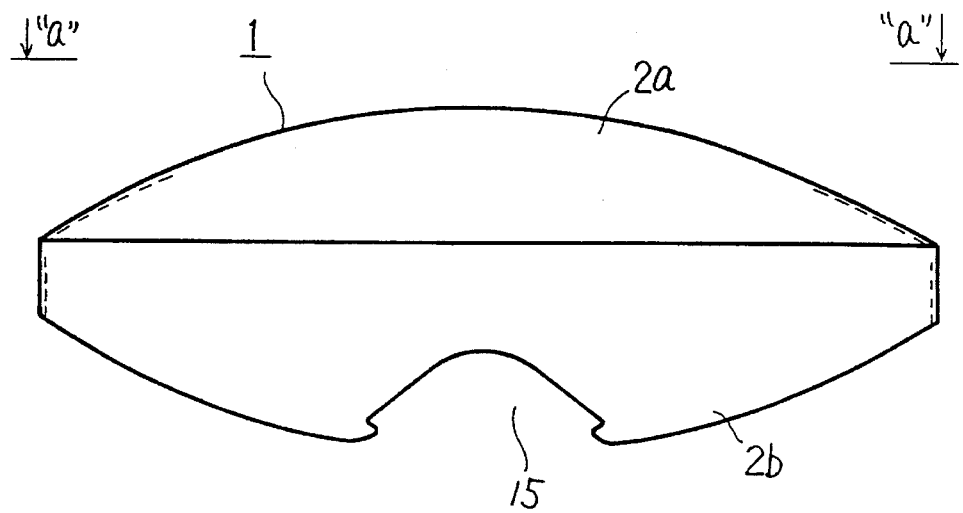
FIG. 2 is a front view of lens 1 in FIG. 1.
Figure 3:
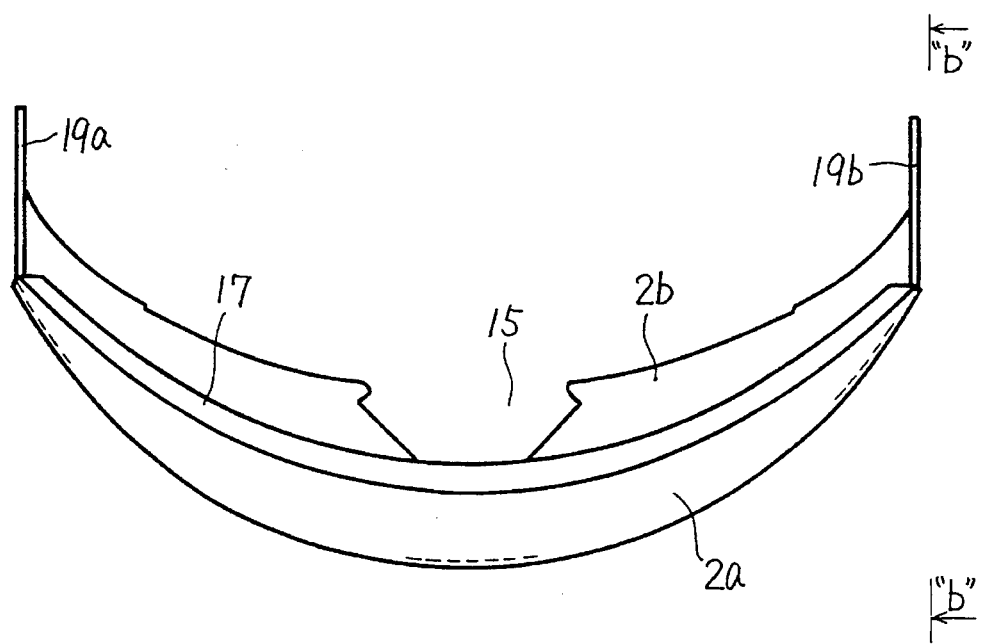
FIG. 3 is a view seen in the direction of arrows "a" in FIG. 2.
Figure 4:
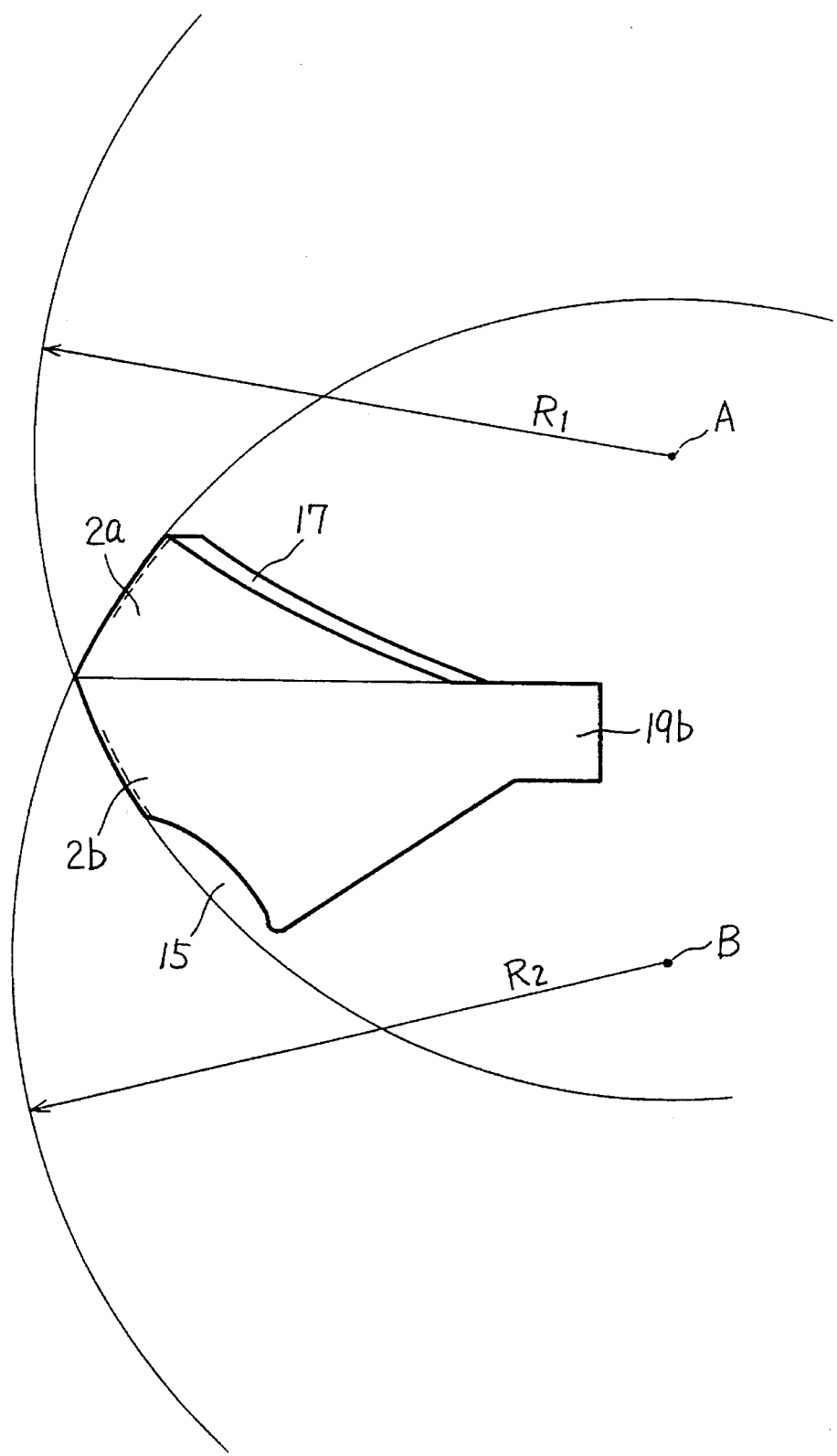
FIG. 4 is a view seen in the direction of arrows "b" in FIG. 3.

FIG. 2 is a front view of lens 1 in FIG. 1, FIG. 3 is a view seen in the direction of arrows "a" in FIG. 2, and FIG. 4 is a view seen in the direction of arrows "b" in FIG. 3.

Referring to these figures, the structure of lens 1 will be described.

Lens 1 is made of a transparent plastic material such as acrylic, and structured by upper and lower lenses 2a and 2b. Upper lens 2a is shaped by a mold corresponding to a portion of a sphere having a radius $R_2$, and lower lens 2b is shaped by a mold corresponding to a portion of a sphere having a radius $R_1$ as shown in FIG. 4. Center positions or center points A, B of respective spheres are deviated from each other. In this embodiment, radius $R_1$ is set to 186 mm and radius $R_2$ is set to 191.5 mm. A nose piece mounting portion 15 for fixing the removable nose piece 3 is formed by removing a lower center portion of lower lens 2b in a triangle shape. Upper lens 2a and lower lens 2b may be fabricated separately and adhered to each other on a boundary surface. In this embodiment, however, in order to obtain a favorable view, a mold is made corresponding to portions of respective spheres, and upper and lower lenses 2a and 2b are formed integrally using such mold.

Although back protruding portions 19a and 19b for fixing support portions 7a and 7b are formed integrally with lower lens 2b, back protruding portions 19a and 19b may be fabricated separately and connected and fixed to lower lens 2b because the field of vision is not particularly significant in these portions.

Effects of setting the eyeglasses, which employs the lenses for eyeglasses according to one embodiment of the present invention, on a user will be described referring to FIGS. 5 and 6.

Figure 5:
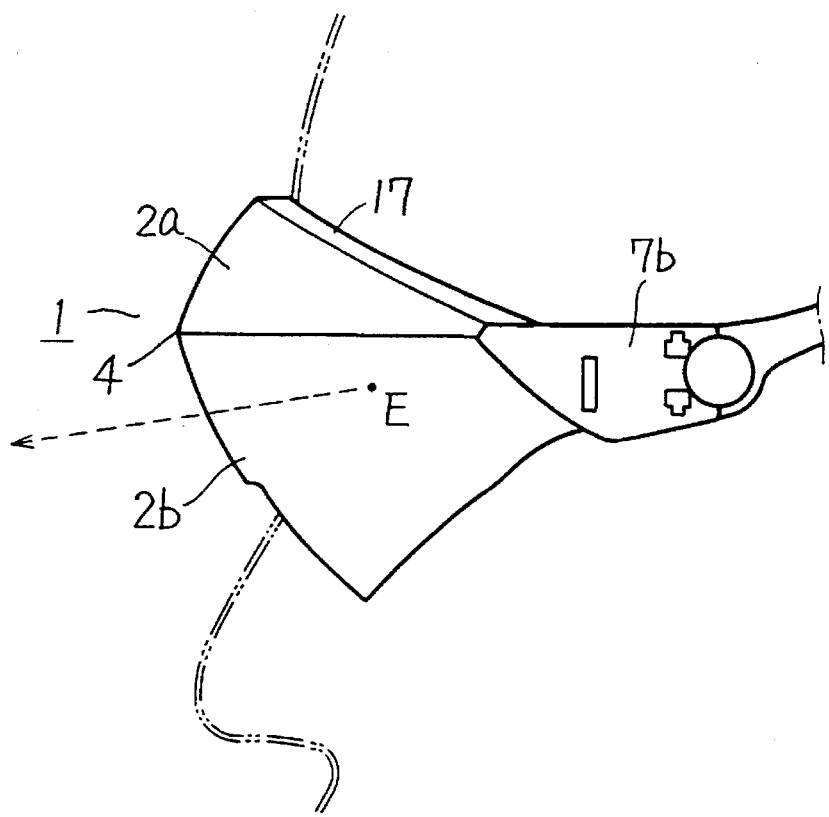
FIG. 5 is a side view showing eyeglasses having a lens for eyeglasses according to one embodiment of the present invention when set on a user.

FIG. 5 is a side view showing eyeglasses having lens 1 according to one embodiment of the present invention when worn by a user in a normal posture. As shown in the figure, a line-of-sight from eye position E of the user is directed forward through lower lens 2b as shown in broken line. The eyeglasses is shown from the side in this figure, but when as apparent from the view of FIG. 3, lower lens 2b constitutes a portion of a sphere and distortion due to the curved surface of the lens is so small. Therefore, a favorable view can be obtained because all the lights coming from objects included in the view come in almost perpendicularly to the surface of lower lens 2b.

Figure 6:
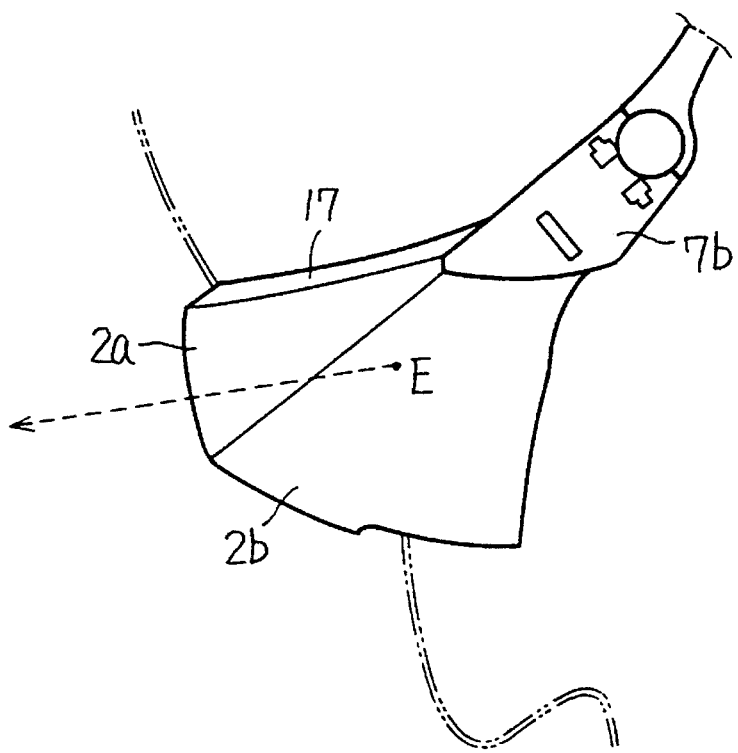
FIG. 6 is a side view showing eyeglasses having a lens for eyeglasses according to one embodiment of the present invention when used while a user bends forward.
Figure 9:
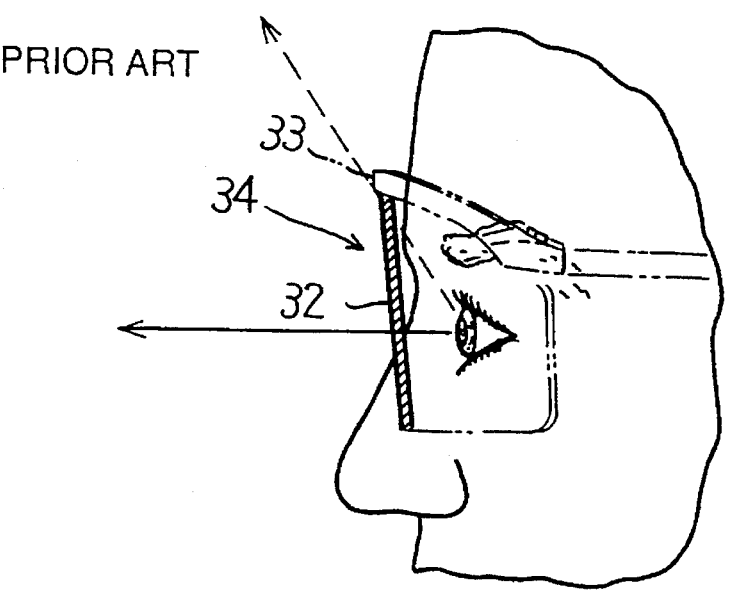
FIG. 9 is a view seen in the direction of arrows "c" in FIG. 8.
Figure 10:
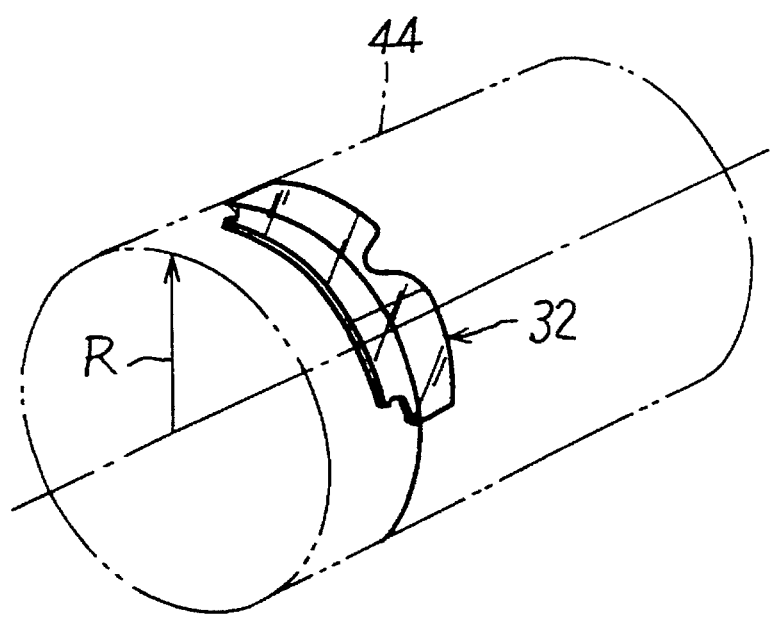
FIG. 10 shows the shape of curved surface of a lens for eyeglasses shown in FIG. 8.

FIG. 6 is a side view showing a state when a user bents forward on a bicycle such as a racer for road race. As shown in the figure, a forward line-of-sight of the user from eye position E is directed along the arrow shown in broken line in such a state. In this case, since the front view is coming into eyes of the user through upper lens 2a, there is nothing interrupting the field of vision compared to the direction shown in broken line in FIG. 9 showing the conventional case, whereby a favorable view can be secured. In addition, associated with the effect of pad 5 in FIG. 1, inflow of air through a space between a forehead and the eyeglasses can be prevented because upper lens 2a is inclined in the direction of the forehead of the user, and therefore so-called watery eye during exercising in sports can be prevented.

Since upper and lower lenses 2a and 2b are shaped integrally using a single mold as described above, a favorable front view can be secured even at a boundary portion. Also, lens 1 has such a shape that a tip portion 4 thereof protrudes forward compared with the conventional lens formed of a portion of outer surface of a cylinder, and thus this is a favorable shape with respect to air resistance, for example, in high speed running.

Both of the upper lens and the lower lens are made of, for example, a transparent plastic in the above embodiment, but the upper lens may be colored for use as sunglasses while using the transparent plastic for the lower lens, whereby the dazzle in the field of vision may be reduced during the normal use.

Figure 7:
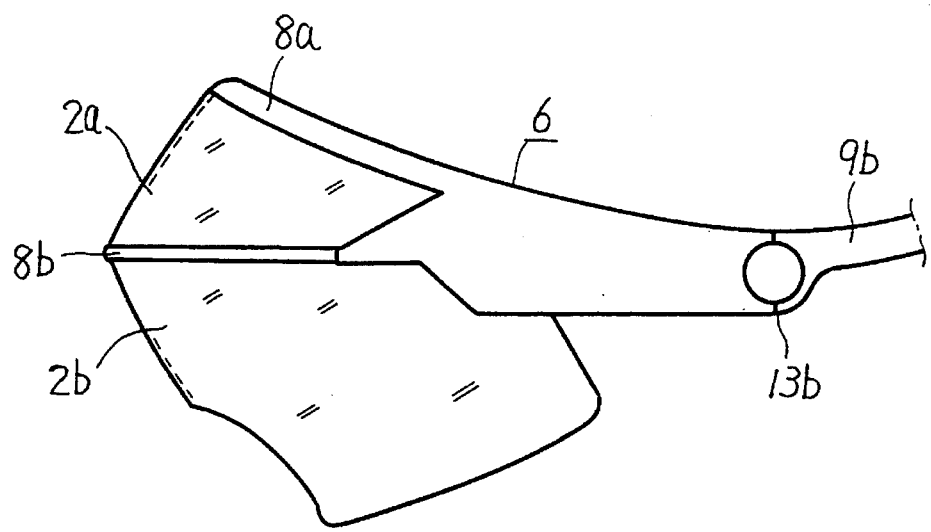
FIG. 7 shows a side structure of eyeglasses according to another embodiment of the present invention.
Figure 8:
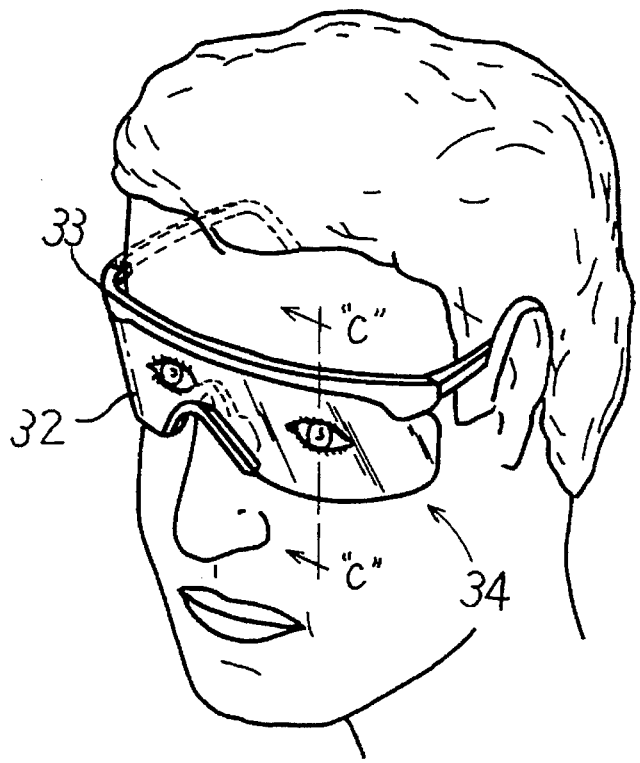
FIG. 8 is a perspective view showing a conventional eyeglasses during use.

FIG. 7 is a side view of sunglasses for use in sports according to another embodiment of the present invention.

Referring to the figure, upper lens 2a which is colored and made of a portion of a sphere is affixed between upper frame 8a and lower frame 8b which constitute a frame 6. Temple 9b is connected via hinge portion 13b at a back portion of frame 6. Meanwhile, lower lens 2b, which is colored and made of a portion of a sphere having a radius different from a radius for upper lens 2a, is affixed to lower frame 8b at its upper portion. Therefore, unlike the previous embodiment, upper and lower lenses 2a and 2b are not formed integrally, but they are formed separately and fixed to each other via frame 6 in this embodiment. Consequently, a manufacturing cost of a spherical lens can be reduced compared to the previous embodiment, and also a wider variety of lenses are available. The transparent plastic may be used only for lower lens 2b for securing the field of vision efficiently.

Although the present invention has applied to the sunglasses for use in sports in the above embodiments, it may apply to ordinary eyeglasses.

The radius of the sphere for the upper lens is different from that of the lower lens in the above embodiments, but the radii may be made identical.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A lens for eyeglasses for use in sports that is integrally formed and has a substantially constant thickness, comprising a first lens formed as one part of said lens and including a first curved surface, a second lens formed as another part of said lens and including a second curved surface, each curved surface having a radius extending from a center point, the center points of said first and second curved surfaces being located on the same side relative to a surface defined by the first and second lenses, each curved surface being a portion of a sphere wherein the radius defining said first curved surface is smaller than the radius defining said second curved surface.

2. The lens for eyeglasses according to claim 1, wherein said first and second lenses are formed integrally using a mold.

3. The lens for eyeglasses according to claim 1, further comprising a supporting frame for mounting temples and having a portion of said lens affixed thereto.

4. The lens for eyeglasses according to claim 3, further comprising a pad formed by an elongate resilient material having a trench, and attached detachably to said first lens via said trench.

5. A lens for eyeglasses for use in sports that is formed in one piece and has a substantially constant thickness, comprising a first lens formed as one portion of said one piece lens and including a first curved surface, a second lens formed as another portion of said one piece lens and including a second curved surface, each curved surface having a radius extending from a center point, the center points of said first and second curved surfaces being located on the same side relative to a surface defined by the first and second lenses, each curved surface being a portion of a sphere, wherein the radius defining said first curved surface is shorter than the radius defining said second curved surface.

* * * * *